(12) United States Patent
Villette et al.

(10) Patent No.: US 8,692,657 B2
(45) Date of Patent: Apr. 8, 2014

(54) WIRELESS CONTROL DEVICE FOR CONTROLLING A SURGICAL APPARATUS

(75) Inventors: Olivier Villette, Andreze (FR); Vincent Guist'hau, Coron (FR)

(73) Assignee: SARL Dentalhitec, Mazieres en Mauges (FR)

( * ) Notice: Subject to any disclaimer, the term of this patent is extended or adjusted under 35 U.S.C. 154(b) by 165 days.

(21) Appl. No.: 13/191,551

(22) Filed: Jul. 27, 2011

(65) Prior Publication Data

US 2012/0028218 A1 Feb. 2, 2012

(30) Foreign Application Priority Data

Jul. 30, 2010 (FR) ...................................... 10 56325

(51) Int. Cl.
*A61C 1/02* (2006.01)

(52) U.S. Cl.
USPC ......... 340/12.5; 433/101; 318/551; 200/86.5; 251/295

(58) Field of Classification Search
USPC ......... 340/12.5; 200/86.5; 251/295; 318/551; 433/101
See application file for complete search history.

(56) References Cited

U.S. PATENT DOCUMENTS

| | | | | |
|---|---|---|---|---|
| 5,340,953 A | * | 8/1994 | Krebs et al. ................ | 200/86.5 |
| 5,635,777 A | * | 6/1997 | Telymonde et al. ........ | 307/119 |
| 5,883,615 A | * | 3/1999 | Fago et al. .................. | 345/156 |
| 6,051,797 A | * | 4/2000 | Meinel ........................ | 200/86.5 |
| 6,179,829 B1 | * | 1/2001 | Bisch et al. ................. | 606/1 |
| 6,639,332 B2 | * | 10/2003 | Metzler et al. ............. | 307/119 |
| 7,428,439 B1 | | 9/2008 | Reynolds et al. | |
| 7,455,520 B2 | * | 11/2008 | Sorensen et al. ........... | 433/98 |
| 7,674,991 B2 | * | 3/2010 | Baird et al. ................. | 200/61.29 |
| 7,883,458 B2 | * | 2/2011 | Hamel ......................... | 600/1 |
| 8,003,905 B2 | * | 8/2011 | Kuehner et al. ............ | 200/86.5 |
| 8,076,599 B2 | * | 12/2011 | Mora .......................... | 200/86.5 |
| 8,294,671 B1 | * | 10/2012 | Hargreaves et al. ....... | 345/157 |
| 2005/0147940 A1 | | 7/2005 | Mace | |
| 2005/0251228 A1 | | 11/2005 | Hamel | |
| 2007/0152508 A1 | * | 7/2007 | Mezhinsky ................. | 307/119 |
| 2007/0166662 A1 | | 7/2007 | Lint et al. | |
| 2007/0254261 A1 | | 11/2007 | Rosenblood et al. | |

OTHER PUBLICATIONS

Republic of France Patent Office, Preliminary Search Report in French Patent Application No. 1056326 (Mar. 21, 2011).

* cited by examiner

*Primary Examiner* — Mohammad Ghayour
*Assistant Examiner* — Nay Tun
(74) *Attorney, Agent, or Firm* — Leydig, Voit & Mayer, Ltd.

(57) ABSTRACT

A wireless control device for controlling, with a human foot, an apparatus for multiple surgical functions. The device includes a base having small dimensions, at least two modules mounted on the base for generating specific control signals for each of the surgical functions, a transmitter for transmitting the control signals, a receiver receiving the control signals, a source of electricity for supplying the transmitter with electrical current, and two actuators, actuated by the human foot and pivotally mounted to act simultaneously on the corresponding module, the transmitter, and the source of electricity. The actuators are pivotally mounted around respective axes that are perpendicular to each other.

7 Claims, 6 Drawing Sheets

WIRELESS CONTROL DEVICE FOR CONTROLLING A SURGICAL APPARATUS

FIELD OF THE INVENTION

The present application relates to a wireless control device for controlling, with a foot, an apparatus for different surgical functions.

BACKGROUND

In the surgical field, in general, and in the field of dental surgery, in particular, practitioners use apparatuses equipped with switches or interrupters which may be actuated with the foot. Indeed, for certain interventions, it is required, or, at the very least, recommended, to use appliances such a, for example, microscopes, UV lamps, and many other appliances, that the practitioner should be able to start, adjust, and stop himself/herself. An example is the focusing and displacement of a microscope by which the practitioner observes the object on which he/she intervenes. As his/her hands are occupied with the gestures of the operation, there only remains the use of the foot for controlling the apparatus.

Thus, pedal controls with one or several pedals have been developed. These controls have been connected to the apparatus to be controlled through a cable and were further connected through another cable to a current outlet or to another type of electricity source.

However, certain operations require that the practitioner be able to move during the operation. In this case, the presence of cables may be bothersome or even dangerous when the practitioner has to move with the apparatus in his/her hand. For this reason, wireless controls were developed. They are designed in order to send radio-electric or optical signals to the apparatus to be controlled which decodes them and carries out the required tasks. An example is described in document U.S. Pat. No. 7,428,439.

But since the interventions may last for a rather long time, one must be sure that the electric power supply of these wireless controls may be ensured during this long period of time.

One means for managing this is to use electronic modules with low electrical power consumption, which consequently have small dimensions. An additional means is to use as a source of electricity means for generating electricity at the moment when the transmitter of the wireless control needs it. Such a source of electricity also has small dimensions.

The problem which is posed for designing a control device meeting the different requirements listed above, consisted of combining miniaturization of the wireless control, strictly speaking, with the robustness and large dimensions required for foot actuation and notably for blind actuation, i.e., without the practitioner needing to concentrate on specifically laying his/her foot on either one of the actuators of the wireless control, so as to not divert his/her attention from the main task, namely the surgical operation.

Indeed, when the device to be controlled only has two functions and is further not subject to constraints in dimensions and energy such as those listed above, a control device with two pedals, mounted one beside the other and spaced from each other, may be actuated without any risk of confusing the pedals, and without risking accidental actuation of one of the actuators at the moment when the other actuator is targeted.

However, when control means of small dimensions have to be actuated by means of members adapted to the dimensions and stiffness of the shoes of a practitioner, the solutions used before the invention are not satisfactory.

SUMMARY OF THE INVENTION

The problem is solved by a wireless control device for controlling, with the foot, an apparatus for multiple surgical functions, the device comprising, mounted on a base, at least two modules for generating a specific control signal for each of the surgical functions, a transmitter for transmitting the control signal to a receiver of the apparatus, and a source of electricity for supplying electrical power to the transmitter, the modules, wherein the transmitter and the electricity source are gathered together in a receiving base of small dimensions, for example with a side of the order of 3-4 cm, and at least two actuators individually actuated by the foot and pivotally mounted for simultaneously acting on the module, the transmitter, and the source of electricity.

According to the invention, both actuators are pivotally mounted around two axes that are perpendicular to each other and a control device comprises a mobile connecting plate interposed between one of the actuators and the base gathering the modules, the transmitter, and the source of electricity.

With the arrangements of the invention it is possible to position two or more actuators so that their tilting or pivot axes are very close to each other, which corresponds to the condition of being able to act on a set of elements of small dimensions, and nevertheless use actuators of large dimensions, the supporting surfaces of which for the foot are sufficiently far from each other so that the practitioner may press on them with his/her foot without any risk of confusion.

Advantageously, one of the actuators is mounted so as to tilt around a first axis and the connecting plate is mounted so as to tilt around a second axis which is different from the first axis and arranged parallel to the first axis. Both axes are then arranged perpendicularly to the axis of the other actuator, or to the axis of each of the other actuators, if, for example, there are a total of three actuators.

In other words, when the control device comprises three or more modules for generating a specific control signal for each of the surgical applications, it comprises a third actuator for directly and simultaneously trigger the corresponding module, the transmitter, and the source of electricity when a specific control signal has to be generated and transmitted to the apparatus. The third actuator is then pivotally mounted around an axis parallel to the axis of the one of the two other actuators which actuates the corresponding module without any interposed connecting plate.

Depending on the selected embodiment of the device of the invention, the actuator, with which is associated the connecting plate, comprises a remote tray acting on the connecting plate to trigger via the corresponding module, the transmitter and the source of electricity, simultaneously, when a specific control signal has to be generated and transmitted to the apparatus.

The base on which the actuators are mounted occupies a surface with a side of the order of 20 cm.

The module(s) for generating a specific control signal for each of the surgical applications, the transmitter, and the source of electricity are either individual means that can be placed together in the receiving base or integrated into a single element or casing, the dimensions of which correspond to those of the receiving base.

By applying the last mentioned characteristic, it is possible to make a compact pedal control device with a risk as small as possible of the practitioner pressing on both pedals at the same time.

BRIEF DESCRIPTION OF DRAWING FIGURES

Other characteristics and advantages of the present invention will become apparent from the description of an embodiment hereafter, with reference to the drawings wherein.

DETAILED DESCRIPTION

Figure 1:
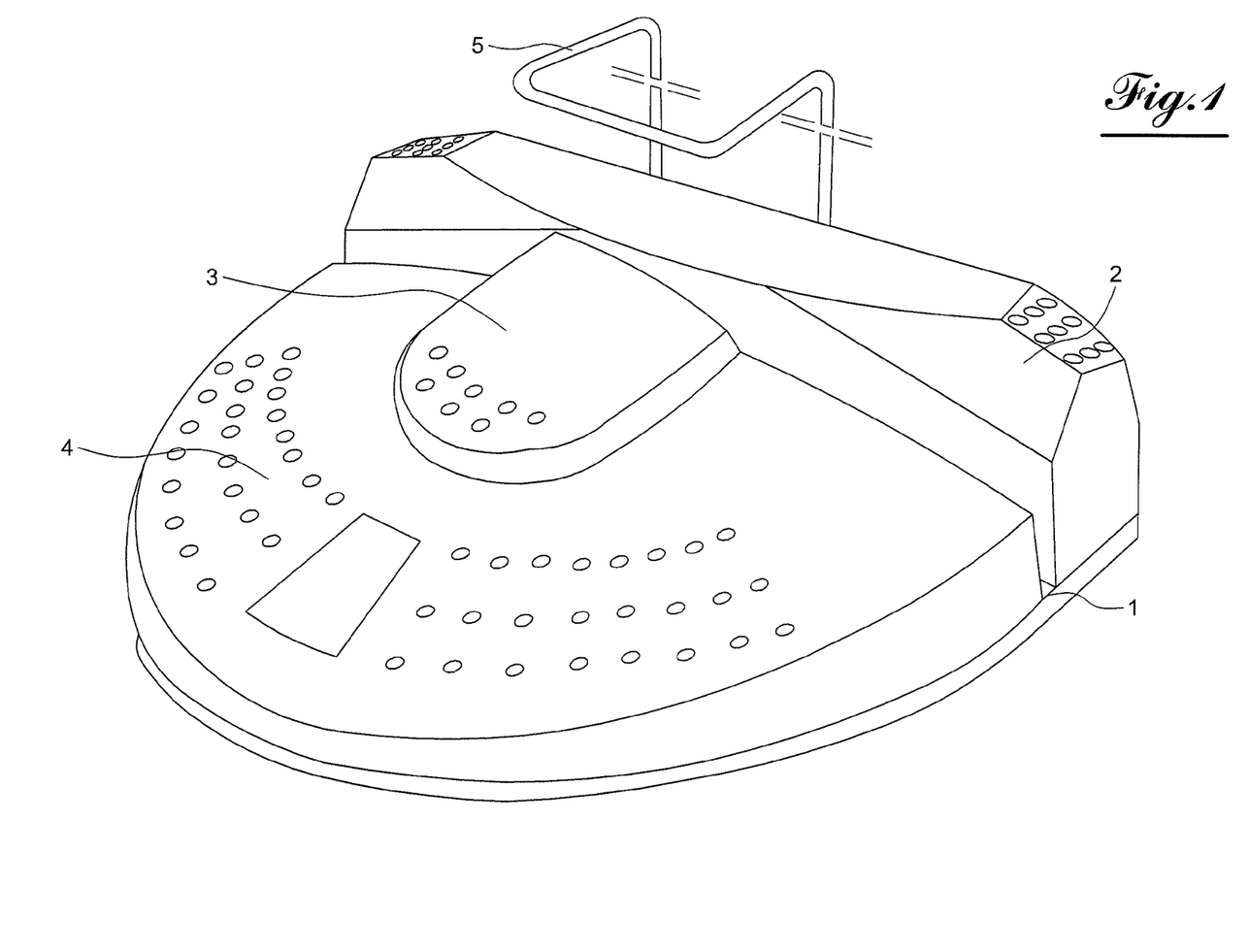
FIG. 1 illustrates, in a three quarter view, an embodiment of the invention in the form of a control device with pedals.

According to the exemplary embodiment illustrated in the drawings, and notably in the assembled condition in FIG. 1, the control device according to the invention comprises a base 1 through which the device of the invention may rest on a floor, a first tilting actuator 2, a second actuator 3, a third actuator 4 pivotally mounted, and a bow 5 attached on the base 1 and allowing a practitioner to displace the control device during an operation by lifting it and transporting with his/her foot. The shape of the control device is approximately that of a body having a semi-circular bottom on which the actuators rise in the form of terraces.

Figure 2:
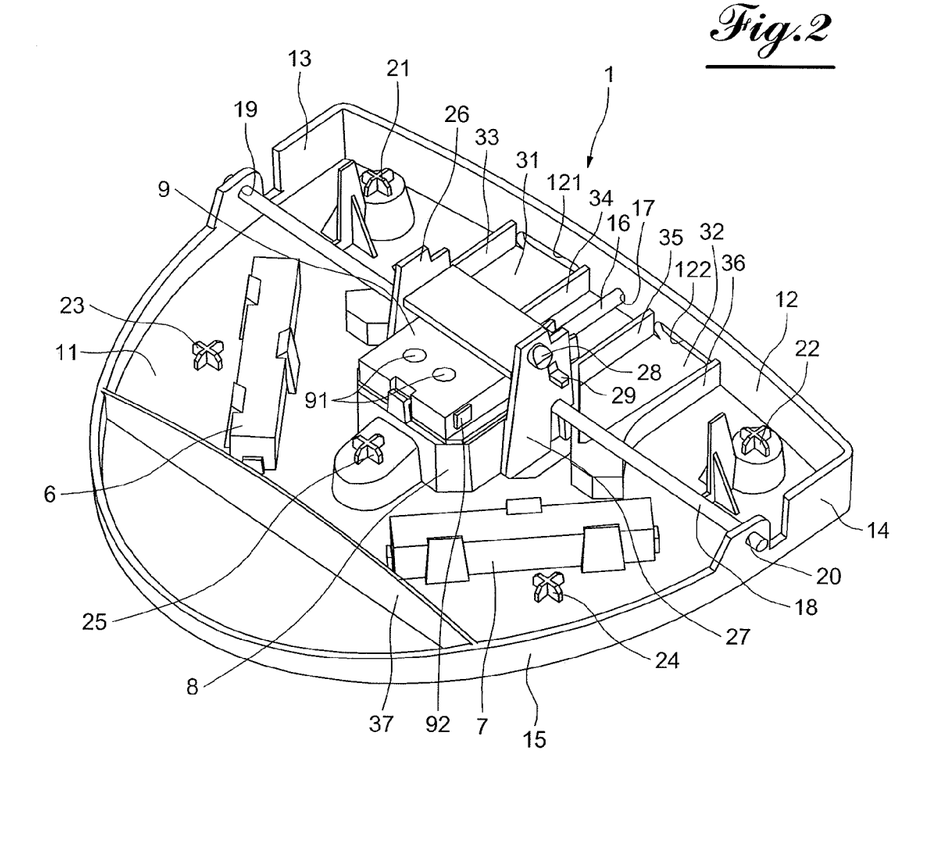
FIG. 2 illustrates the bottom element of the device of the invention.

As shown by FIG. 2, the base 1 essentially has the shape of a semi-circular bottom plate 11 with a slightly curved rear edge 12, two approximately planar left 13 and right 14 side edges and a curved front edge 15, the height of which is less than that of the three other edges 12 to 14.

Let us note in this context that the orientation indications such as front, rear, high, and low appearing in the present description refer to the position of use of the device as visible in FIG. 1.

The base advantageously comprises, but not necessarily, masses 6, 7 having sufficient weight for giving the control device, notably when the base and the actuators are made of a plastic material, a good stable base, avoiding as far as possible any untimely displacement of the control device.

The base 1 also comprises an internal base 8 for receiving an electronic unit 9 which allows an electrical control signal to be generated and transmitted towards an apparatus controlled by this control device. This unit 9 is actuated by the actuators 2 to 4, as this will be described later on.

The base 1 further comprises an axle 16 through which the actuator 2 is mounted to the base 1 so as to be able to tilt over and an axle 18 through which the actuator 4 is pivotally mounted to the base 1. The axle 16 is inserted in two orifices, one of which, referenced as 17, is located in the rear wall 12 of the base 1 and the other one of which (not shown) is located in a rear wall of the internal base 8. The axle 18 is inserted into two orifices 19, 20 located in the side walls 13, 14 of the base 1. Now it is immediately seen that the axle 16 is perpendicular to the axle 18.

According to an alternative not shown, the tilting actuator 2 may be replaced with two actuators pivotally mounted in opposite directions around two axes arranged perpendicularly to the axle 18. Such an arrangement, although more complex than the described embodiment, would allow a compact design of the control device of the invention.

The base 1 moreover comprises supports 21, 22 for helicoidal springs (not shown) putting the actuator 2 back into the rest position when the practitioner does not press on it, supports 23, 24 for helicoidal springs (not shown) putting the actuator 4 back into the rest position, and a support 25 for a helicoidal spring (not shown) putting the actuator 3 back into the rest position.

The base 1 finally comprises two arms 26, 27 rising perpendicularly upwards on the bottom 11 and each having an upper protrusion and a lower protrusion. The upper protrusions, FIG. 2 only showing the protrusion 28 of the arm 27, are used together as a pivot axle for the actuator 3. And the lower protrusions, FIG. 2 only showing the protrusion 29, are used as upward movement limiters when the actuator 3 is pushed into the rest position by the corresponding spring. According to the illustrated embodiment, the arms 26, 27 are placed side-by-side at the internal base 8.

In order to be able to attach the bow 5 on the base 1, the rear wall 12 of the latter is provided with two apertures 121, 122 through which the bow is introduced. The free ends of the bow 5 are then housed in spaces 31, 32 respectively defined by ribs 33, 34, and 35, 36. A rib 37, approximately parallel to the rear wall 12 of the base 1 is used for limiting the downward tilt of the actuator 4.

Figure 3:
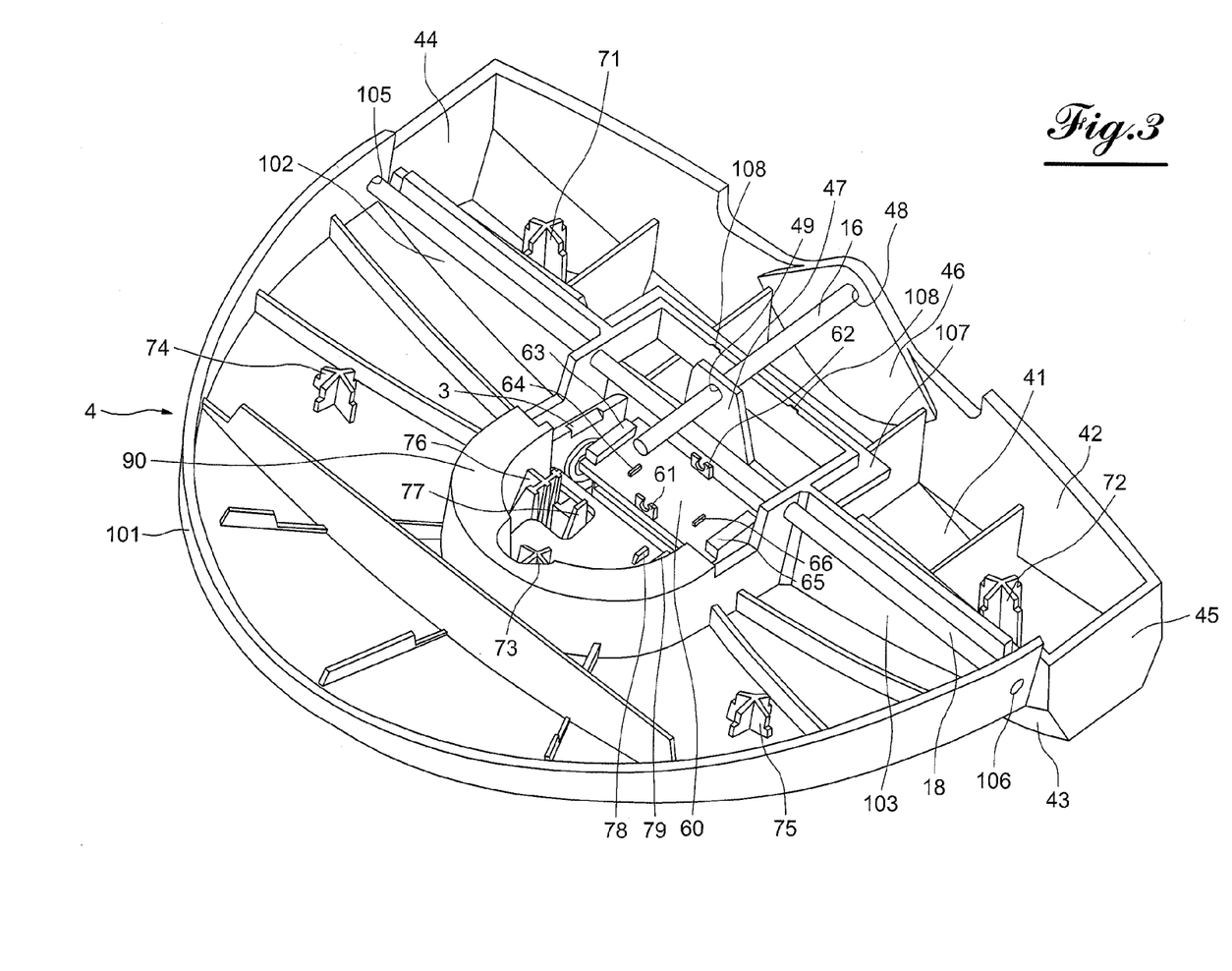
FIG. 3 illustrates the actuators in a three quarter view from the inner side of the device.

FIG. 3 illustrates the actuators 2 to 4 from below, i.e., upside down, showing their lower faces in a mounting arrangement with the axles 16 and 18 respectively for the tilting of the actuator 2 and for the tilting of the actuator 4. Each of these three actuators includes a hollow body, opening downwards, with a wall, i.e. upper surface, on which the practitioner presses with his/her foot and with side walls depending from the upper surfaces.

Figure 4:
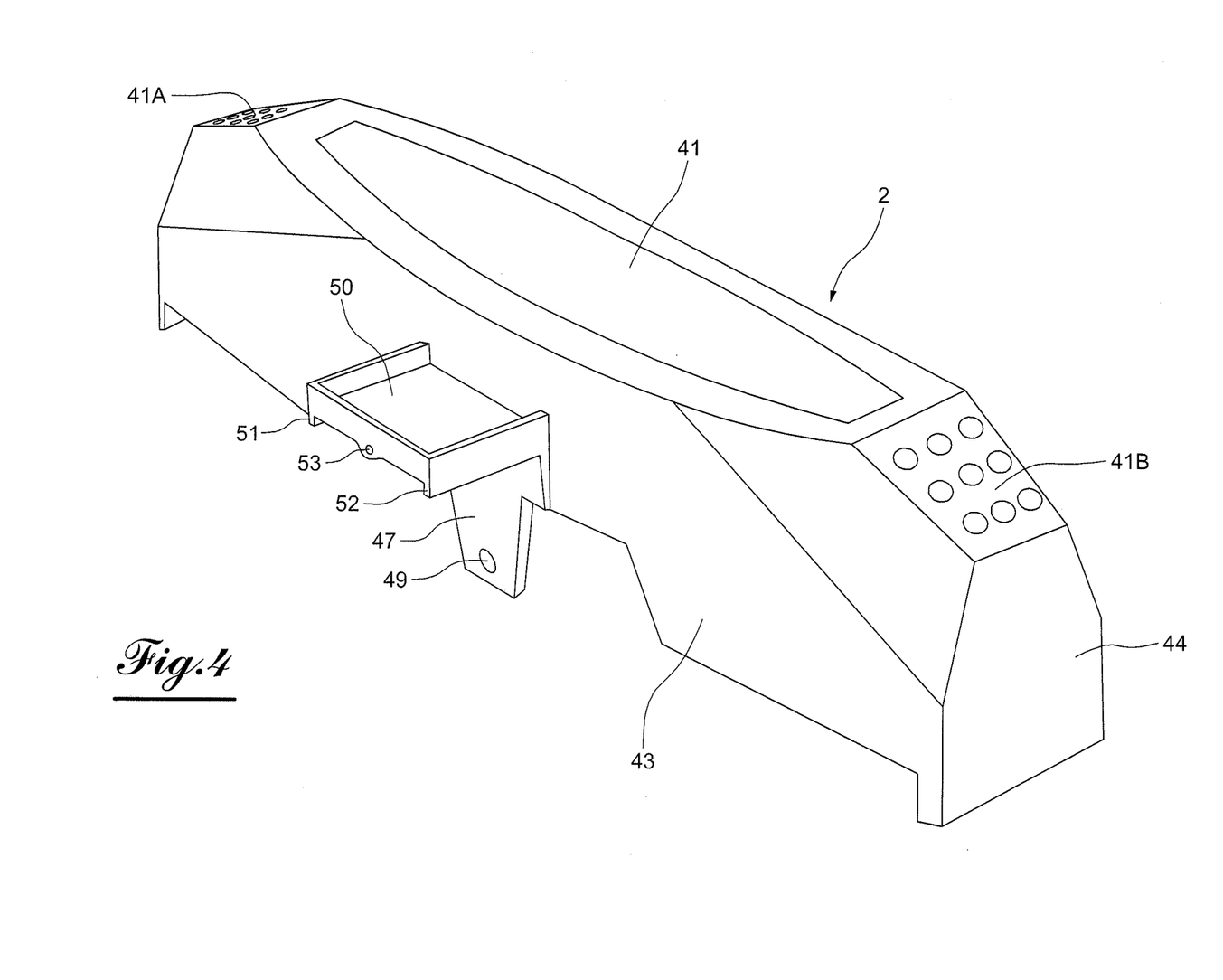
FIG. 4 illustrates the tilting actuator in a three quarter view.

Thus, as shown in more detail in FIG. 4, the tilting actuator 2 comprises an approximately planar supporting wall 41 with, on the upper face, supporting surfaces 41A, 41B on which the practitioner presses for triggering a control signal. The actuator 2 further comprises rear wall 42, front wall 43, right wall 44 and left wall 45 which approximately extend perpendicularly from the wall 41. The rear wall 42 and front wall 43 are provided with protrusions 46, 47 in which are made orifices 48, 49 receiving the axle 16.

The actuator 2 also comprises a remote tray 50 extending horizontally from the front wall 43 and including on its lower face, ribs 51, 52 formed at the ends of the tray and oriented parallel to the axle 16, as well as a central rib 53 also oriented parallel to the axle 16.

A connecting plate 60 bears on its lower face two central profusions 61, 62, which form the tilting axis of this plate, ribs 63, 64 on one side of the tilting axis and ribs 65, 66 on the other side. The connecting plate 60 is matched with the tray 50. It is through these ribs that the actuator 2/connecting plate 60 assembly acts on the electronic unit 9 in order to trigger control signals, as explained with reference to FIG. 5.

Indeed, in order to obtain a compact control device while minimizing the risk that the practitioner accidentally presses on two actuators at one time, the device comprises an electronic unit 9 laid out in a casing having length and width of the order of 3 to 4 cm while the control device occupies a surface with a side of the order of 20 cm. According to the embodiment illustrated, the electronic unit 9 comprises four modules, each module having a pair of contactors for generating a specific control signal for each of the provided surgical functions of the controlled apparatus. Two of these four modules are illustrated by two contactors 91 that are visible in FIG. 2 and by two contactors 92. Only one of the contactors 92 is visible in FIG. 2, the other contactor 92 being located on the opposite side of the electronic unit 9 from the visible contactor 92. A further pair of modules, including respective pairs of contactors 91 and 92, connected upon the tilting of the actuator 2, as described below, are not visible in the figures because of the presence of other elements of the control device that obscure those two modules of the electronic unit 9.

In order to trigger respective modules of the electronic unit 9, the actuator 2/connecting plate 60 assembly and each of the actuators 3, 4 include means to press on a pair of the contactors 91 and 92 of a respective one of the modules. These means are basically visible in FIG. 3 for actuators 3 and 4 and illustrated in detail in FIG. 5 for actuator 2.

Figure 5:
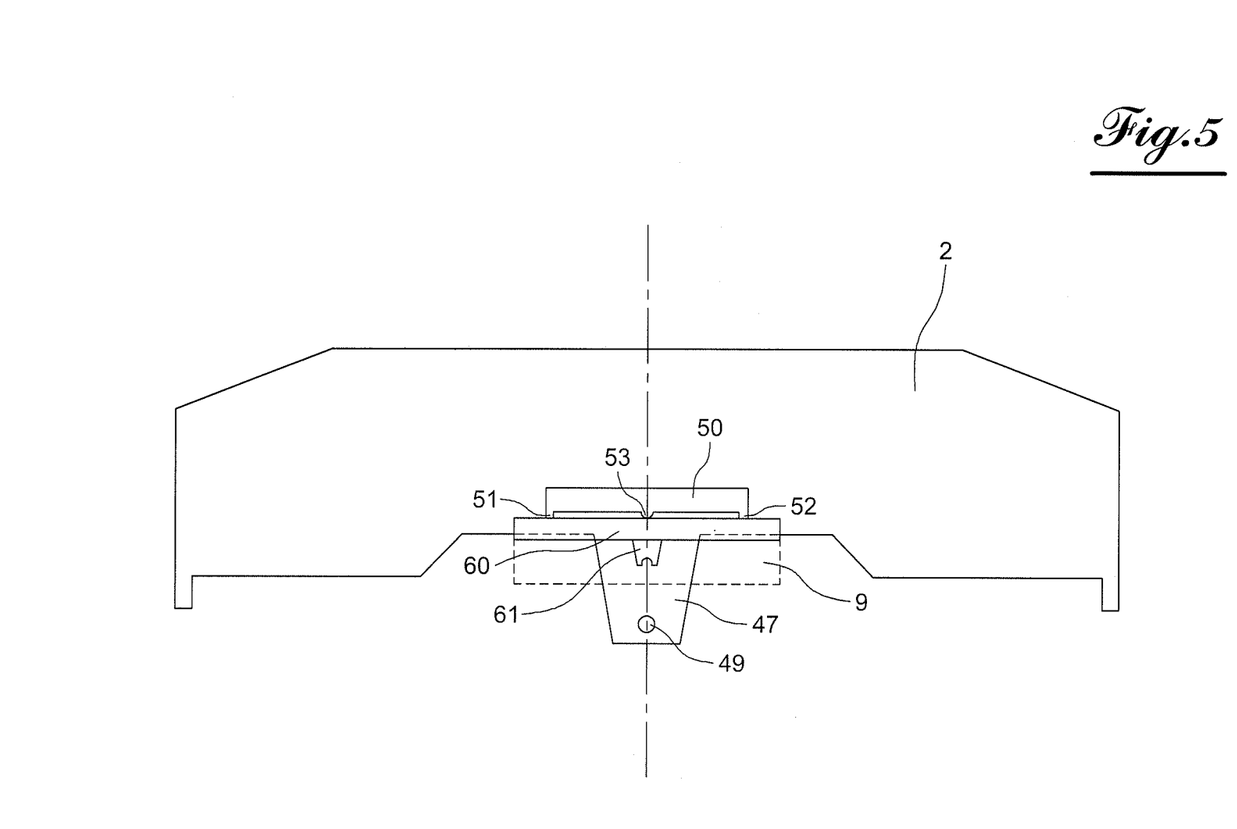
FIG. 5 is a front view of the tilting actuator of the device of the invention.

FIG. 5 illustrates the tilting actuator 2/connecting plate 60 assembly in a front view in the mounting position with respect to the electronic unit 9. This figure more particularly shows the position of the axle 16 of the tilting actuator 2 and protrusions 61, 62 of the connecting plate 60.

As it is not reasonably possible to superpose, even in a terrace arrangement, more than two actuators, in this case, the actuators 3 and 4 dedicated to the signal generating contactors 91, a solution had to be found in order to actuate both of the rear signal generating modules which are not visible in the figures. The solution found is the one visible in FIGS. 2 and 3, i.e., orient the axle of the actuator 2 perpendicular to the axles of the actuators 3, 4 and to place the actuator 2 immediately behind the actuator 4.

According to the illustrated embodiment, the rear modules are indirectly actuated by a respective one of the two opposite ends of the tilting actuator 2.

Indeed, the actuator 2 does not act itself on the rear modules, but by the off-axis arrangement of its axle 16, i.e., moves the plate 50 to and fro along a path in the form of a circular arc. In this way, the tray 50 slides on the connecting plate 60 and causes it to tilt in one direction or the other. Thus, by pressing on the right end of the tilting actuator 2, the tray 50 slides towards the right and causes the connecting plate 60 to tilt towards the right, which causes the ribs 63, 64 to press on the contactors 91 and 92 of the right rear module, of the electronic unit 9, i.e., one of the modules that is not visible in FIG. 2. Likewise, the fact of pressing on the left end of the actuator 2 causes the connecting plate 60 to press on the contactors 91 and 92 of the left rear module of the electronic unit 9, i.e., one of the modules that is not visible in FIG. 2. The return of the actuator 2 to the rest position is ensured by two helicoidal springs (not shown) maintained between the supports 21, 22 of the base 1 and corresponding supports 71, 72 on the lower face of the wall 41 of the actuator 2.

Figure 6:
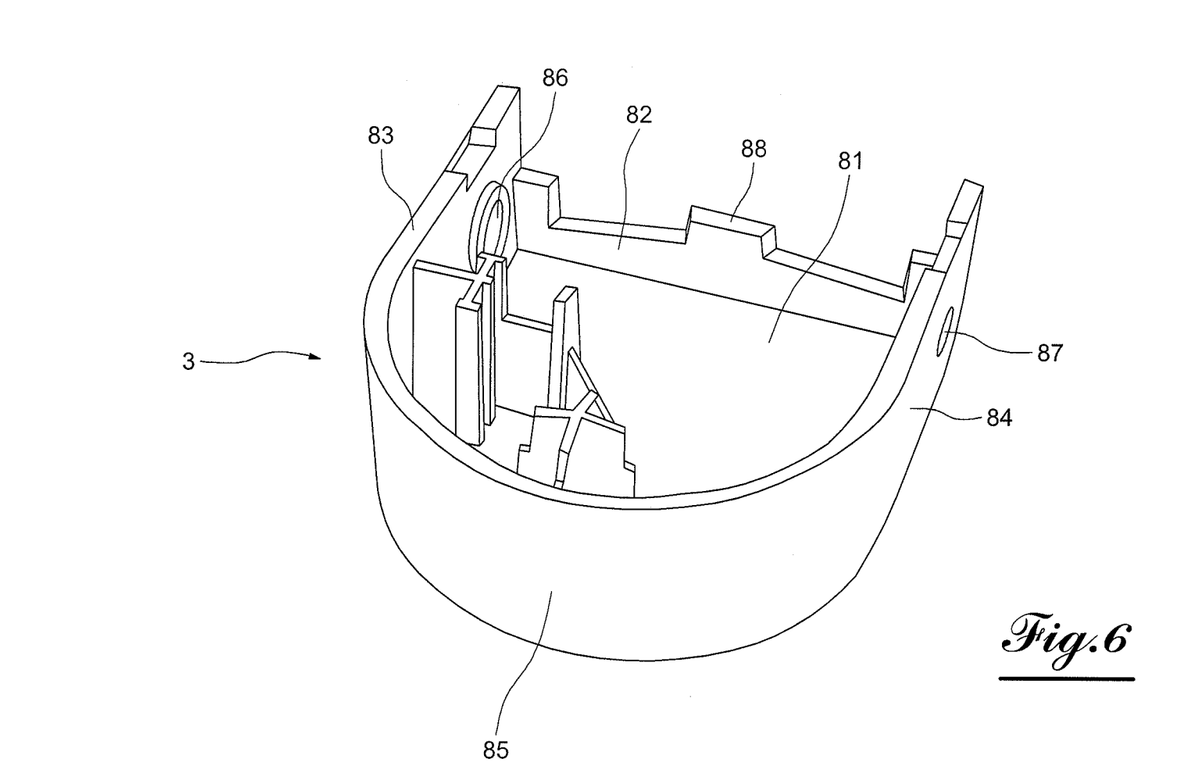
FIG. 6 illustrates the central actuator in a three quarter view from the inner side of the device.

As shown in more detail in FIG. 6, the actuator 3 comprises an approximately planar supporting wall 81 on which the practitioner presses in order to trigger a control signal. The actuator 3 further comprises a rear wall 82, two approximately planar side walls 83, 84 and a curved front wall 85 which approximately extend perpendicularly from the wall 81. The side walls 83, 84 are provided with orifices 86, 87 receiving the protrusions 28 of the arms 26, 27 of the base 1. The protrusions 28 form the pivot axis of the actuator 3. The actuator is also provided with a central protrusion 88 extending downwards from the rear wall 82 and used as an additional limiter of an upward movement, in addition to the protrusions 29 of the arms 26, 27, when the actuator 3 is pushed into the rest position by the spring. In the rest position of the actuators 2 and 3, the protrusion 88 remains slightly above the upper face of the tray 50 of the tilting actuator 2.

The actuator 3 directly acts on the contactor 91 on the right front module of the electronic unit 9, as seen in FIG. 2, and is superposed to the actuator 4 which directly acts on the of the left front module of the electronic unit 9 as seen in FIG. 2. Consequently, the actuator 3 does not include any ribs simultaneously acting on the contactor 91 and the corresponding contactor 92 but has fingers 76, 77 for this purpose and located inside the actuator 3. According to the illustrated embodiment, but by no means in a limiting way, the fingers 76, 77 extend from the wall on which the practitioner presses, perpendicularly downwards inside the actuator 3 and cross the actuator 4 through an aperture provided for the purpose. Return to the rest position of this actuator is ensured by a helicoidal spring (not shown) maintained between the support 25 of the base 1 and a support 73 of the actuator 3.

As shown in more detail in FIG. 3, the actuator 4 comprises a supporting wall 101 on which the practitioner presses in order to trigger a control signal. The actuator 4 further comprises rear walls 102, 103 interrupted by a bow 107 and a curved front wall 104 provided on the left and right sides, close to the rear walls 102, 103, with orifices 105, 106 receiving the pivot axle 18.

The actuator 4 includes, in its middle, a wide and arched groove 90 (seen from below in FIG. 3), the shape and the dimensions of which receive the actuator 3 therein. In order to directly act on the contactors 91, 92 at the left front signal generating module of the electronic unit 9, as seen in FIG. 2, the actuator 4 is provided with a rib 78 and with staging 79.

The return to the rest position of this actuator is ensured by a helicoidal spring (not shown) maintained between the supports 23, 24 of the base 1 and the supports 74, 75 of the actuator 4.

The bow 107 is a possible embodiment of an upward movement limiter intervening, by bearing upon the ribs 34, 35 of the base 1, when the actuator 4 is pushed into the rest position by the springs. Optionally, the bow 107 may be provided with protrusions 108 extending here and there the bow downwards.

As regards the use and the operation of the control device, the practitioner may individually press on each end of the tilting actuator 2 and on the actuators 3 and 4 with the same position of the device close to the floor and without any risk of inadvertently pressing on both actuators at the same time. Further, the electronic unit 9 and, more particularly, each of the signal generating modules, may be programmed in different ways in order to be able to generate more different signals than there are modules in the unit 9. Thus, for example, the signal generated by a module may vary according to the number of times the practitioner presses rapidly on the corresponding actuator. The presented example of four signal generating modules is therefore not to be considered as a limitation. Subsequently, each signal is forwarded towards the transmitter which is powered by the source of electricity simultaneously with the module or with a slight shift.

The invention claimed is:

1. A wireless control device for controlling, with a human foot, an apparatus for performing a plurality of respective surgical functions, the control device comprising:
   a base having a bottom plate with a bottom side for being supported on a floor and a top side, opposite the bottom side, wherein the base plate has a rear edge and a front edge that is at least partially opposite the rear edge;
   first and second axles mounted on the base, parallel to and spaced from the top side of the base plate, and perpendicular to each other;
   a front actuator having a top surface and located proximate the front edge of the base plate, wherein the front actuator is pivotally mounted on the first axle so that the first actuator can be actuated by a human foot pressing on the top surface of the first actuator;
   a rear actuator having a top surface and located proximate the rear edge of the base plate, wherein the rear actuator is pivotally mounted on the second axle so that the second actuator can be actuated by a human foot pressing on the top surface of the rear actuator, and the top surface of the rear actuator is farther from the top side of the base plate than is the top surface of the front actuator;

an internal base located on the top side of the base plate and having a surface generally parallel to the top side of the base plate; and an electronic unit comprising at least two modules for generating respective control signals for respective surgical functions of the apparatus, wherein the electronic unit is located on the surface of the internal base, and at least the front actuator, when pivoted, controls operation of a first of the at least two modules of the electronic unit.

2. The control device according to claim 1, including a structure mounted on the base and providing a third axle spaced from the top side of the base plate and parallel to the first axle;

an intermediate actuator having a top surface and located between the front and rear actuators, wherein the intermediate actuator is pivotally mounted on the third axle so that the intermediate actuator can be actuated by a human foot pressing on the top surface of the intermediate actuator, and the intermediate actuator, when pivoted, controls operation of a second of the at least two modules of the electronic unit.

3. The control device according to claim 2, wherein the top surface of the intermediate actuator is farther from the top side of the base plate than is the top surface of the front actuator, and the top surface of the rear actuator is farther from the top side of the base plate than is the top surface of the intermediate actuator.

4. The control device according to claim 2, wherein the front and intermediate actuators independently control operation of the first and second modules of the electronic unit.

5. The control device according to claim 1, wherein the rear actuator comprises a connecting plate tiltingly mounted with respect to the base plate and tilting around the second axle, and elements protruding from the connecting plate toward the base plate for controlling operation of two of the modules of the electronic unit, depending upon direction of pivoting of the rear actuator about the second axle with respect to a central rest position of the rear actuator.

6. The control device according to claim 5, wherein the rear actuator comprises a tray extending above the connecting plate with respect to the base plate.

7. The control device according to claim 1, wherein the internal base has sides along the top surface of the base plate that are 3 cm to 4 cm in length.

\* \* \* \* \*